United States Patent [19]

Hill et al.

[11] Patent Number: 5,057,306
[45] Date of Patent: Oct. 15, 1991

[54] METHOD OF MANUFACTURING ORAL HYGIENE GELS

[76] Inventors: Ira D. Hill, Clay Ct., Locust, N.J. 07760; Robert D. White, 65 Glen Grey Rd., Oakland, N.J. 07436

[21] Appl. No.: 535,912

[22] Filed: Jun. 8, 1990

Related U.S. Application Data

[63] Continuation-in-part of Ser. No. 927,725, Nov. 6, 1983, and a continuation-in-part of Ser. No. 927,805, Nov. 6, 1986, Pat. No. 4,950,479.

[51] Int. Cl.$^5$ .......................... A61K 7/16; A61K 7/30
[52] U.S. Cl. ...................................... 424/49; 514/835; 514/901; 514/944; 424/56; 239/350; 222/402.1; 222/402.12; 222/424.5
[58] Field of Search ........................... 424/49, 56, 439; 514/901, 835, 944; 239/350; 222/402.1, 402.12, 424.5

[56] References Cited

U.S. PATENT DOCUMENTS

| | | | |
|---|---|---|---|
| 1,411,681 | 4/1922 | Burlew | 424/49 |
| 1,633,336 | 6/1927 | Larson | 424/49 |
| 2,004,957 | 6/1935 | Messner | 424/455 |
| 2,024,146 | 12/1935 | Crowther | 424/49 |
| 2,031,233 | 2/1936 | Stillwell | 424/551 |
| 2,089,845 | 8/1937 | Atkins | 424/49 |
| 2,677,700 | 5/1954 | Jackson et al. | 568/618 |
| 2,778,045 | 1/1957 | Bly et al. | 15/198 |
| 3,228,845 | 1/1966 | Najjar | 424/49 |
| 3,431,339 | 4/1969 | Gyarmathy et al. | 424/52 |
| 3,475,533 | 10/1969 | May | 424/57 |
| 3,574,824 | 4/1971 | Echeandia et al. | 424/50 |
| 3,639,563 | 1/1972 | Januszewski | 424/49 |
| 3,907,991 | 9/1975 | Accetta | 424/49 |
| 3,928,618 | 12/1975 | Bauman | 424/49 |
| 3,929,988 | 12/1975 | Barth | 424/54 |
| 3,947,570 | 3/1976 | Pensak | 424/54 |
| 3,949,939 | 4/1976 | Brown | 239/350 |
| 3,957,964 | 5/1976 | Grimm, III | 424/10 |
| 4,011,309 | 3/1977 | Lutz | 424/49 |
| 4,069,312 | 1/1978 | Mannura | 424/49 |
| 4,071,614 | 1/1978 | Grimm, III | 424/49 |
| 4,130,636 | 12/1978 | Tomlinson | 424/49 |
| 4,143,126 | 3/1979 | Gaffar | 424/49 |
| 4,343,785 | 8/1982 | Schmolka | 424/49 |
| 4,420,472 | 12/1983 | Boden | 424/58 |
| 4,446,157 | 9/1984 | Boden | 426/3 |
| 4,465,661 | 8/1984 | Schmolka | 424/49 |
| 4,465,663 | 8/1984 | Schmolka | 424/62 |
| 4,476,107 | 10/1984 | Schmolka | 424/49 |
| 4,511,563 | 4/1985 | Schmolka | 514/162 |
| 3,9765,765 | 8/1976 | Nachtigal | 424/54 |

FOREIGN PATENT DOCUMENTS 0075410 4/1985 Japan .

OTHER PUBLICATIONS

The Merck Index, 9th ed., Merck & Co., Inc., Rahway, N.J., 1976, Citations 6971 and 7349.
Afseth, Caries, Res., 17:472-475 (1983).
Bowden, Com Dent. Assoc. J., 50, p. 169, (1984).
Harrap et al., Archs. Oral Biol., vol. 29, No. 2, pp. 87-91 (1984).
Harrap et al., Journal of Peridontal Research, 18:634-642 (1983).
Havensar, J. Dent. Res., vol. 63, No. 2, pp. 120-123 (1984).
Hayes, J. Dent. Res., vol. 63, No. 1, pp. 1-5 (1984).
Jari, Advances in Pharmacology and Chemotherapy, vol. 20, pp. 191-218 (1984).
Loesche et al., Jada, vol. 108, pp. 587-592 (1984).
Makkinen et al., Jada, vol. 111, pp. 745-751 (1985).
Mordenti et al., Journal of Pharmaceutical Sciences, vol. 71, No. 12, pp. 1410-1421 (1982).
Segal et al., Journal of Pharmaceutical Sciences, vol. 74, No. 1, pp. 79-81 (1985).
Southard et al., Jada, vol. 108, pp. 337-441 (1984).
Topitsglou et al., Caries, Res. 17: pp. 369-378 (1983).
Winter et al., Caries, Red. 16: pp. 349-352 (1982).
Jakush, Jada, vol. 109, pp. 690-702 (1984).
Fine et al. Journal of Chemical Peridontology, 12: pp. 660-666 (1985).
J. Navia, The Biologic Basis of Dental Caries, Chapter 14 (heading only), Lewis Menaker, Harper and Row (1980).
Maybell, The Biologic Basis of Dental Caries, Chapter 5, (heading only), Lewis Menaker, Harper and Row (1980).
Morhart and Fitzgerald, the Biologic Basis of Dental Caries, Chapter 11 (heading only), Lewis Menaker, Harper and Row (1980).
Morhart et al., The Biologic Basis of Dental Caries, Chapter 12 (heading only), Lewis Menaker, Harper and Row (1980).
Alfano, The Biologic Basis of Dental Caries, Chapter 16 (heading only), Lewis Menaker, Harper and Row (1980).
Caufield and Navia, The Biologic Basis of Dental Caries, Chapter 18 (heading only), Lewis Menaker, Harper and Row (1980).
Makkinen et al., Ann. Rev. Nut., vol. 2, pp. 133-150 (1982).
J. Am. Dent. Assoc., vol. 109, 690 ff (1984).
Bhasker et al., Comp. Contin. Educ. Dent. Suppl., 5, pp. 587-593 (1984).
van Houton et al., Rev. Infect. Dis., vol. 5, Suppl. 4, pp. 5659-5669 (1983).
van Houton et al., J. Infection, vol. 10, No. 4, pp. 252-260 (1982).

*Primary Examiner*—Ronald W. Griffin
*Attorney, Agent, or Firm*—Ernest V. Linek

[57] ABSTRACT

The invention relates to the manufacturing of oral hygiene gels wherein a coating substance is emulsified with a surfactant using a hot-melt emulsion process and the resulting emulsion is subsequently gelled with a viscosifier.

13 Claims, No Drawings

METHOD OF MANUFACTURING ORAL HYGIENE GELS

CROSS-REFERENCE TO RELATED APPLICATIONS

This application is a continuation-in-part of copending application Serial Numbers: 06/927,752, filed Nov. 6, 1986 and 06/927,805, filed Nov. 6, 1986, Now U.S. Pat. No. 4,950,479, the disclosures of which are hereby incorporated herein by reference.

FIELD OF THE DISCLOSURE

The invention relates to the manufacturing of oral hygiene gels suitable for cleaning plaque-like films from the gums of babies and endentulous persons and includes the steps of holt-melt emulsifying a coating substance in a nonionic surfactant followed by gelling said hot-melt emulsion with a viscosifier.

BACKGROUND OF THE INVENTION

Major advances have been made in the control of dental caries and gum disease. For example, a recent National Institute of Health, (NIH) survey reported that over 50% of all U.S. school children have no cavities. The concern over caries has been replaced by the concern for gum disease. Recently, various plaque fighting and tartar control oral care products have been successfully marketed in the U.S. The emergence of these products and their sales success confirm the increased awareness of plaque, gingivitis and gum disease among adults. This increased awareness and concern over plaque, gum disease and oral care in general is now carrying over to the care of baby teeth and gums, by those parents who are aware of gum disease.

Historically, the care of baby teeth was not a major concern of parents. Pediatric dental care usually started in the home about the time a youngster could brush his or her teeth and expectorate. This usually occurred about the time the full set of baby teeth were developed, usually between the ages of 2 and 3.

The NIH has sought to raise the awareness level among parents of the need to start caring for their baby's teeth and gums prior to teething and up through the time the child itself can effectively control the plaque formation on their teeth by regular brushing. In their pamphlet, *A Healthy Mouth For You and Your Baby*, the NIH states:

"Clean your baby's teeth. Baby teeth collect plaque just like adult teeth and need to be cleaned too, to prevent decay and gum disease. Usually the baby's first teeth are the two lower front ones, followed by the two upper front ones. As soon as the first tooth appears, simply wipe it with a clean washcloth or gauze pad. As more teeth appear, brush them with a soft brush gently and carefully every day.

By the time the baby is two and a half years old, all the baby teeth will probably be in the mouth. About this time, children can begin using their own soft toothbrush with a very small amount of fluoride toothpaste (no more than the size of a pea) but because your children cannot remove plaque, you should continue to brush your child's teeth until about the age of seven."

In his publication "*Early Intervention: Prenatal and Postnatal Counseling and Infant Dental Care*", Arthur Nowak suggests: "The parent should be responsible for cleaning the infant and young child's teeth, until the time when the child can do it by himself." The author continues: "In order to clean the newly erupting teeth of the very young infant, the parent can wrap gauze around the finger, then rub the gum pads and the teeth. As more teeth erupt into the mouth, the parent should use a small, soft bristled brush."

Most pediatricians agree: A dentifrice should not be employed until the child and the parent have developed a cleaning routine and are comfortable with it, particularly expectorating. It is generally accepted that: Early use of an adult dentifrice can cause a negative reaction in some young children because of foaming action and flavor. Note: the foaming action of the dentifrice not only causes gagging but also decreases visibility in the child's mouth.

Most pediatricians today recommend that even before the baby teeth have erupted, the parent should select a time during the day when the infant's mouth can be inspected and a gauze wrapped finger inserted to clean the gums. This kind of early involvement will accustom the child to the cleaning process that is necessary for good infant oral hygiene.

Historically, teething was defined as the "eruption" or "cutting" of the teeth. Today, most researchers agree that this eruption of teeth is not a cutting process, and therefore should not be painful to the infant nor should it be responsible for the symptoms historically associated with teething i.e., increase in irritability, loss of appetite, change in bowel habits, wakefulness, some rash, fever, dribbling and drooling. All of these symptoms, historically associated with teething, can be attributed to other factors and thus, may not be caused by teething, per se.

It has been suggested by some pediatric dentists that the discomfort associated with teething can be minimized and in some cases prevented if the parent will begin cleaning baby's gums when teeth first appear under the surface as bumps. For example, Stephen Moss DDS, MS, New York University professor and past president of the American Academy of Pediatric Dentistry suggests: "Cleaning the gums helps, because plaque—an accumulation of sticky micro-organisms in the mouth—can be an irritant to baby when it builds up on gums pads. Remove the plaque, and you remove a major cause of teething pain. Begin cleaning baby's gums once you see teeth growing under the gums, usually around six to ten months."

Heretofore, the irritated gums of babies observed during teething have been traditionally treated with various surface analgesic products such as benzocaine containing substances that are rubbed onto the gums for the purpose of imparting temporary relief in the form of a "numbing" action. These products do not clean the gums, nor do they disrupt formation of the plaque-like coating on the soft tissue. Moreover, many young mothers express concern over their baby ingesting a drug such as benzocaine. Additionally, the relief obtained with these products is only temporary, less than an hour and more typically about 30 minutes, and the child appears to continue to be in pain generally exhibiting symptoms of discomfort and irritability. Numerous home remedies have been reported for relief of teething discomfort and include rubbing "wine" and/or paragoric on the gums and around the teeth, during "fussy" periods.

There is some concern that the amount of finger pressure required to effectively remove the plaque-like buildup from a baby's gums with a gauze can often times be troublesome to the baby. Moreover, it is difficult to thoroughly clean all the "bumps and valleys" in the infants gums that are encountered just prior to tooth eruption with a gauze alone. Generally, this type of cleaning is perceived as an unpleasant experience for the baby as well as by the parent doing the cleaning.

Dr. Walter Loesche, in his chapter "Decline in S. mutans Associated Caries Secondary to Medical Usage of Antibiotics", in *Molecular Microbiology and Immunology of S. mutans,* 1986, S. Hamada et.al.; presented convincing evidence that reducing the microbial count during teeth eruption is important. The author suggests, the emerging teeth and tissues are far more vulnerable to colonization by the organisms most frequently cited for tooth decay. General oral cleanliness including frequent removal of food residuals and reduction of the total bacterial count in the mouth by frequent cleaning of the soft tissues and the emerging teeth would be an effective non-antibiotic means of controlling colonization by these organisms.

The literature further has established that:
1. *S. mutans,* plaque formers, are found in all samples of microflora obtained from babies with erupted teeth.
2. *S. mutans* are generally associated with primary infection.
3. Removal of the plaque-like film reduces teething pain.
4. Cleaning the gum pads help the first teeth arrive in a clean plaque-free environment and reduces teething pain.
5. With less acid in the infants mouth (produced by *S. mutans*) the infant will have an easier time teething.

The gums of endentulous persons, similar to babies, also require regular cleaning and massaging for optimum health, sense of well being and prosthesis comfort.

24% of Americans 65 and older have lost all their teeth. The number of endentulous patients seeking initial treatment in the year 2000 is projected at 10.4 million Americans compared to 9.0 million in 1980, thus, in spite of improved oral care, endentulism continues to increase.

There is a need for endentulous subjects to massage their gums regularly. According to Dr. Cali in his book, *The New Lower-Cost Way to End Gum Trouble without Surgery,* 1982, i.e., "The gums, like muscles, benefit from a massage. They need to be exercised, toughened and ensured a good blood supply". "Good circulation, the continued replacement of exhausted blood and nutrients with fresh blood and nutrients, prevents disease more effectively than any drug."

Dr. N. T. Nguyen in his text *Your Mouth, Oral Care for All Ages.* 1979, states: "Proper hygiene is absolutely essential for maintaining healthy gums in denture wearers. Twice a day remove the dentures and massage the gum tissue with a soft brush or a wash cloth moistened in water. This massage will stimulate the circulation and maintain the health of gums."

There is therefore a definite need in the art for a product such as an oral hygiene gel suitable for cleaning, massaging and conditioning the gums of babies and endentulous persons.

In view of the foregoing it is an object of this invention to provide oral hygiene gels for the cleaning, massaging and conditioning of gums.

It is also an object of this invention to provide oral hygiene gels suitable for cleaning, massaging and conditioning the gums of babies and endentulous persons, including those adults with some natural teeth remaining.

It is a further object of the invention to provide improved methods for cleaning, massaging and conditioning gums of babies and endentulous persons.

It is still a further object of the invention to provide methods for relieving the discomfort normally associated with teething as well as the discomforts of the gums experienced by endentulous persons.

It is yet another object of this invention to provide an improved method of manufacturing the oral hygiene gels of the invention.

SUMMARY OF THE INVENTION

In accordance with the foregoing objectives, this invention provides oral hygiene gels intended for cleaning, massaging and conditioning of gums of babies and endentulous persons to relieve the discomfort associated with teething and the wearing of dentures. The oral hygiene gels of the present invention comprise a cleaning/massaging/conditioning preparation containing a surfactant, a coating substance and a viscosifier. The gels of the present invention are free from abrasives, analgesics and substances that alter the microflora balance of the oral cavity. These gels can be characterized as: stable, ingestible, non-foaming and substantive to the gums of babies and endentulous persons as well as disruptive towards the "plaque-like" films that tend to form on these gums.

DETAILED DESCRIPTION OF THE INVENTION

The oral hygiene gels of this invention are ingestible non-foaming preparations which are free from: alcohol, analgesics such as benzocaine, and abrasives such as those generally used in dentifrices. These gels comprise a nonionic surfactant, a coating substance insoluble in said surfactant, and a viscosifier. These gels are particularly suited for cleaning plaque-like films from the gums of babies and endentulous persons and for conditioning these gums and disrupting the formation of plaque-like films on these treated gums. The gels of the present invention are substantive to the gums of babies and endentulous persons.

The term gel, as used in the present invention, is defined as a "jelly-like substance formed by a suspending agent, wherein the solid and liquid phases appear continuous."

The term ingestible, as used in the present invention, is defined as "capable of being ingested with no risk of danger to the baby and/or endentulous persons ingesting the gels of the present invention."

Endentulous persons, as used in the present invention, is defined as "persons who have lost all of their natural teeth or have lost a sufficient quantity of their natural teeth such that a prosthesis is required."

Non-foaming, for purposes of the present invention, is defined as "producing little or no foam during application of the gel to gums, such that the foaming, if any, will not cause discomfort or gagging to the baby or endentulous person."

Free from alcohol, for purposes of the invention, is defined as "containing no ethanol or similar substance or containing trace amounts of same such that the characteristic burning sensation that accompanies alcohol is not perceived by the user of the gels of the present invention."

Free from abrasives, for the purposes of the present invention, is defined as "containing no abrasive, nor abrasive like substance such as the silicas and phosphates generally used in some dentifrices, or containing trace amounts of these substances such that their characteristic abrasive action cannot be perceived by the user of the gels of the present invention."

The nonionic surfactants, suitable for use in the gel of the present invention include block copolymer mixtures of polyoxyalkylene compounds, i.e., poloxamers including ethylene oxide and propylene oxide poloxamer mixtures; such as those described in U.S. Pat. Nos. 4,343,785; 4,465,663; 4,511,563; and 4,476,107. Commercial versions of these nonionic poloxamer surfactants are available from BASF - Wyandotte Co., Wyandotte, MI and include various Pluronics such as Pluronic F108 and F127 and those Pluronics described in "Pluronic & Tetronic Surfactants", BASF Corp, 1987, at page 2. Other suitable nonionic surfactants useful in the gels of the present invention include polyoxyethylene sorbitan monoleate (Polysorbate 80); polyethylene glycols (Pluracols); nonylphenol ethoxylates (Surfonics); linear alcohol ethoxylates and polyethyleneglycolparaisooctypheny/ethers (Triton's).

The nonionic surfactants in the gels of the present invention are preferably employed at levels ranging from about 0.1% to about 10% by weight of the composition, and most preferably from about 0.5% to about 4% by weight of the gels of the invention. However, in general, the amount of nonionic surfactant employed can be adjusted to provide the desired degree of cleaning and conditioning of the gums desired.

In the present invention, a coating substance is employed in combination with the nonionic surfactant component of the gel. The coating substances suitable for use in the gels of the present invention are insoluble in the surfactant and can be characterized as follows, they:

1. suppress the tendency of the surfactant to foam,
2. are safely ingestible at the concentration used,
3. have an affinity for gum surfaces,
4. are neutral, inert and do not support microbiological activity,
5 modify the surface energy properties of gums such that it is more difficult for food particles, cellular debris and various plaque precursors and formers to attach to these surfaces,
6. form a thin, transparent coating that does not buildup on the gums and is removed by the normal clearing and flushing action of the mouth,
7. impart a pleasant "smooth" feeling to the gums, and
8. retain various flavors and substances on surfaces of gums, imparting an unexpected prolonged flavor effect.

Suitable coating substances for the gels of the present invention include various silicones insoluble in the nonionic surfactants used in the present invention including polyalkysiloxanes such as polydimethysiloxanes, such as Dow Corning 360 Medical Fluid (viscosities of 20 to 12,500 centistokes); Dow Corning Q7-2587 Simethicone Emulsion; Dow Corning 200 Fluids, (60,000 to 100,000 centistokes) with the chemical composition $CH_3SiO[SiO(CH_3)_2]_nSi-(CH_3)_3$; all available from Dow Corning, Midland, MI.

The coating substances of the gels of the present invention are preferably employed at levels ranging from about 0.01 to about 0.5% by weight of the composition; and most preferably from between about 0.05 and about 0.25% by weight of the gel. In general, the amount of coating substances employed is adjusted to provide the desired degree of conditioning and substantivity desired.

The weight ratio of nonionic surfactant to coating substance in the gels of the present invention range from between about 20:1 to about 2:1 and preferably from between about 17:1 to about 3:1.

The viscosifiers suitable for the gels of the present invention include those viscosifiers suitable for gelling the surfactant/coating substance mixtures of the present invention. These include various cellulose gums such as carboxymethy/cellulose (CMC). These anionic, water soluble polymers derived from cellulose are available commercially from Aqualon Company and described as sodium carboxymethy/ cellulose. They are described in detail in "Aqualon Cellulose Gum", Aqualon Company, 1988. Also various hydroxypropy/cellulose, nonionic water-soluble polymers available commercially as Klucel from the Aqualon Company. These are described in detail in "Klucel Hydroxypropy/cellulsoe" Oct, 1987. Further viscosifiers suitable for the gels of the present invention include; cellulose ethers available commercially as Methocel from the Dow Chemical Company and described in detail in "Methocel Cellulose Ethers", Technical Handbook #192-1062-88-JB, Dow Chemical Company.

The viscosifiers suitable for the gels of the present invention are preferably employed at levels ranging from about 0.5 to about 10% by weight of the composition, and most preferably from between about 1.5 to about 6.0% by weight of the gel. In general, the amount of viscosifier employed is adjusted to provide the desired gel properties sought for the purposes of the present invention.

The combination of certain nonionic surfactants with certain coating substances in a gel, wherein the latter is insoluble in the former and the gel cleans, massages and conditions gums of babies and endentulous persons to remove plaque-like films that tend to form on these gums and to disrupt the subsequent formation of such plaque-like films on said gum surfaces is novel. The relief from teething discomfort and denture discomfort experienced when these gels are regularly applied to the gums of babies and endentulous persons is unexpected.

Furthermore, the gels of the present invention do not foam, are free from abrasives and analgesics. They can be used without discomfort, gagging, etc, and they can be swallowed and do not need to be rinsed from the surfaces of the gums. The gels of the invention are substantive to the gums of children and endentulous persons and when not rinsed away they tend to remain and disrupt the subsequent formation of plaque-like films onto the surfaces of gums.

The "plaque-like" film that tends to form on the gums of babies, prior to and during teething, and on the gums of endentulous persons who generally wear prosthesis is believed to include bacteria in a polysaccharide matrix. In some denture wearers this film is considered a contributing factor to Candida yeast infections. In children experiencing teething, this plaque-like film is identified as a host substrate for *S. mutans* and has been suggested as a major contributor to teething discomfort. This discomfort is described as a "gingivitis-like" condition that occurs on the bumps of the baby's gums prior to and during teething.

Most commercial products available today for control of plaque and gingivitis rely on antimicrobial, and antibacterial and/or astringent properties to control these bacterial colonies. Such products can not be used with babies who can not expectorate. Moreover, these commercial products have non-specific, broad-spectrum bactericidal properties and tend to disrupt the critically balanced flora in a baby's mouth. Such disruption of the flora on a regular basis could prove more harmful than the gingivitis condition being treated and is generally not recommended by pediatricians.

The regular cleaning, massaging and conditioning of gums of babies as well as endentulous persons, with the gels of the present invention using a finger, a gauze wrapped finger or a soft bristled brush effectively removes the plaque-like film from the tender gums, massages the gums and leaves a coating on the gums that conditions the gums and disrupts the formation of such plaque-like films later on.

The reduction in teething discomfort achieved with regular use of the gels of the present invention and the method of treating the gums of the present invention should also be accompanied by a reduction in dental caries that is generally associated with plaque buildup on babies gums, as well as reduce other oral disorders generally associated with plaque buildup.

The reduction in plaque-like buildup on the gums of denture wearers achieved with the gels and methods of treating the gums of the present invention should reduce some of the discomfort normally associated with denture wearing as well as improve the health and muscle tone of the gums of denture wearers. Regular massaging of the gums of endentulous persons with the gels of the present invention would reduce the frequency of denture adjustment and generally improve the fit and comfort of dentures and the cleanliness of the gums. Additionally, the removal of "plaque-like" films from the surfaces of the gums will dramatically reduce "denture breath" a condition that generally accompanies the wearing of dentures.

The cleaning of plaque-like film from the gums of babies and endentulous persons with the gels of the present invention is achieved with a minimum of mechanical action and without foaming. After the cleaning step with babies there is no need to expectorate nor to rinse the mouth. The coating that remains on the baby's gums leaves the gums feeling smooth and clean. This coating contains an appropriate flavorant, such that the cleaning/massaging/ conditioning exercise is a pleasant experience which encourages compliance, i.e., regular cleaning.

The film remaining on the gums of babies and endentulous persons is not metabolizable by resident oral cavity microorganisms and is substantive to the surface of the gums. This is to be contrasted with natural film formers such as lecithin which are also substantive to the gums but which are metabolizable and support biological activity. See for example, Menaker, *The Biologic Basis of Dental Caries,* Chapter 16, Gibbon and Hoote, *Ann Rev. of MICROBILOGY.* 29, pp. 19–44; and Hayes, *J. Dent. Res* 632. pp. 2–5.

The coating that remains on the gums after applying the gels of the present invention is inert and is substantive to the gums. As long as this film remains on the gums it:

1. disrupts the subsequent formation of "plaque-like" films on the gums,
2. imparts a smooth feeling, and
3. prolongs the pleasant perception of the flavorant used in the gel. This prolonged flavor perception is particularly novel and unexpected and is a critical contributing factor in the high compliance profile of the gels of the present invention with babies as well as endentulous persons.

Cleaning of an infants gums should start once teeth growing under the gums appear as bumps, usually around age six to ten months. Preferably the gel of the invention is applied to a two-inch square gauze pad that is wrapped around the finger. Slight pressure is applied to the gums as the gel is rubbed over the surfaces of the gums. Such cleaning is recommended twice daily, morning and night. When the first molars appear a small soft-bristled brush usually replaces the gauze pad and teeth are brushed at least once a day but preferably twice, morning and night.

According to the American Dental Association, "Regular cleaning and massaging of yours gums with a soft bristled brush is as important as cleaning your dentures." Preferably a pea size quantity of the gel of the present invention is placed onto a brush or an index finger and then the gum on the lower left side of the mouth is thoroughly cleaned, massaged and conditioned. This step is repeated with a second pea size application of the gel to the gum on the lower right side of the mouth. These steps are repeated with the left and right sides of the upper gum. The user can expectorate if necessary, but it is not necessary to rinse. This process is to be repeated prior to and after wearing dentures. For best results this cleaning, massaging and conditioning is carried out for 30 seconds to 1 minute at least twice a day.

High compliance potential is a critical element of the gels of the present invention. That is, the pleasant mouth feel and low foaming properties of these gels and the prolonged pleasant taste and mouth feel that remains after using the gels of the present invention encourages regular use of the gels of the invention. There is a "it's working" perception of the gels of the invention without negative medicinal connotations which tend to reduce usage and lower compliance potential.

Additional adjuvants can be included in the gels of the present invention including:

a. natural sweeteners such as sorbitol-70. Lycasan (hydrogenated glucose syrup) and xylitol powder in concentrations ranging from between about 10 and about 40 percent by weight.

b. artificial sweeteners such as sodium saccharin and Nutrasweet$^R$ in concentrations from between about 0.05 and about 0.2 percent by weight.

c. humectants such as glycerine, propylene glycol and mixtures thereof at concentrations from between about 5 and about 20 percent by weight.

d. preservatives such as methylparabenz, propyl parabenz, potassium sorbate, sodium benzoate, and mixtures thereof in concentrations from between about 0.05 and about 0.25 percent by weight.

A buffering ingredient may also be added to the gels of the invention in order to prevent natural degradation of the flavoring components. Generally, the pH of these gel compositions is adjusted to between about 3.0 and about 8.5, preferably from about 4.5 to about 6.5. The buffering ingredients such as a weak organic acid such as a weak organic acid such as citric acid or an alkali metal salt of a weak organic acid, for instance, sodium benzoate, sodium citrate, sodium phosphate, or potassium tartrate is generally added in an amount of about 0.1 to about 1.0 percent by weight.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLES

The following examples provide a synopsis of oral hygiene gel preparations of the invention and illustrate the unexpected results obtained by the use of the gels disclosed herein.

EXAMPLE 1

Several gel formulations of the present invention suitable for the cleaning and massaging of babies gums were prepared. These gels had the following general formulation where percentages are by weight:

| Component | Percent |
|---|---|
| Pluronic F-127 | 2.00 |
| Silicone 1500 | 0.12 |
| Sorbital 70 | 34.00 |
| Glycerine | 5.00 |
| Propylene glycol | 10.00 |
| Flavor | 0.75 |
| Methyl Parabenz | 0.15 |
| Propyl Parabenz | 0.05 |
| Potassium Sorbate | 0.15 |
| Sodium saccharin | 0.075 |
| Citric acid | 0.17 |
| Viscosifier | (Type and concentration varies as discussed below). |
| Deionized water | Balance |

A mixing vessel was charged with water, sorbital 70, potassium sorbate, methyl parabenz, propyl parabenz, sodium saccharin and citric acid while stirring with an overhead mixer. The vessel was heated to 60° C. and the contents transferred to a Waring Blender.

In a separate vessel, Pluronic F-127 and Silicone 1500 were heated and stirred to effect a hot-melt emulsion. Flavor was added to the hot-melt emulsion and the flavored, hot-melt emulsion was then added to the mixture in the Waring Blender.

A mixture of propylene glycol/glycerin was stirred while the specific solid viscosifying agent of choice was added to form a suspension. (These are described in detail below). This suspension was added slowly to the Waring Blender with vigorous agitation (390 watts). After 15 minutes the Waring Blender was stopped and the resultant gel was poured into tubes or jars for storage use.

Using the procedure and general formula described above, various viscosifiers were used at one or more concentrations to prepare a series of gels suitable for cleaning and massaging baby gums. Specifically: Klucel GF was used at 5% by weight; Methocel K4M at concentrations ranging from 0.5% to 3.3% by weight; CMC 7LF at concentrations from 5 to 10% by weight; CMC9M31F at concentrations from 1 to 3% by weight and CMC7MF at concentrations ranging from 2 to 4% by weight.

All of these formulations of the present invention were useful as baby gum and teeth cleaners.

Further Examples illustrative of various gels of the present invention suitable for cleaning and massaging baby teeth and gums are set forth in Table I.

TABLE I

| EXAMPLE # | SURFACTANT | (%) | COATING COMPOSITION | (%) |
|---|---|---|---|---|
| 2 | Pluronic F-127 (solid) | .5 | Medical Emulsion AF | 0.10 |
| 3 | Pluronic F-127 (solid) | 1.0 | Dow 1500 | 0.05 |
| 4 | Pluronic F-127 (solid) | 2.0 | Dow 1500 | 0.10 |
| 5 | Pluronic F-127 (solid) | 3.5 | Dow 1500 | 0.20 |
| 6 | Pluronic F-127 (solid) | 2.0 | Dow 1500 | 0.02 |
| 7 | Pluronic F-127 (solid) | 2.0 | Dow 1500 | 0.05 |
| 8 | Pluronic F-127 (solid) | 2.0 | Dow 1500 | 0.20 |
| 9 | Pluronic F-127 (solid) | 2.0 | Dow 1500 | 0.50 |
| 10 | Pluronic F-127 (solid) | 2.0 | Dow 200 cs 100 | 0.10 0.10 |
| 11 | Pluronic F-127 (solid) | 2.0 | Dow 200 cs 350 | 0.10 |
| 12 | Pluronic F-127 (solid) | 2.0 | Dow 200 cs 1000 | 0.10 |
| 13 | Pluronic F-127 (solid) | 2.0 | Dow 360 Med.cs 12,500 | 0.10 |
| 14 | Pluronic P85 (paste) | 2.0 | Dow 1500 | 0.10 |
| 15 | Pluronic P85 (paste) | 1.0 | Dow 360 Med cs 12,500 | 0.10 |
| 16 | Pluronic L64 (liquid) | 2.0 | Dow 1500 | 0.10 |
| 17 | Pluronic L64 (liquid) | 1.0 | Dow 200 cs 100 | 0.05 |

| EXAMPLE # | NATURAL SWEETENER | (%) | ARTIFICIAL SWEETENER | (%) |
|---|---|---|---|---|
| 2 | Sorbitol 70 | 35 | Sodium saccharin | .08 |
| 3 | Sorbital powder | 25 | Sodium saccharin | .10 |
| 4 | Sorbitol 70 | 40 | | .05 |
| 5 | Sorbitol 70/ Lyasan | 25/5 | | .10 |
| 6 | Lycasan | 35 | Nutrasweet | .10 |
| 7 | Sorbitol 70 | 30 | Nutrasweet | .10 |
| 8 | Xylitol powder | 25 | Nutrasweet | .10 |
| 9 | Sorbitol 70 | 30 | Nutrasweet | .10 |
| 10 | Sorbitol 70 | 40 | Sodium saccharin | .05 |
| 11 | Sorbitol 70 | 30 | Sodium saccharin | .10 |
| 12 | Xylitol powder | 20 | Sodium saccharin | .20 |
| 13 | Sorbitol powder | 20 | Sodium saccharin | .08 |
| 14 | Sorbitol 70 | 40 | Sodium Saccharin | .05 |
| 15 | Sorbitol 70 | 30 | Sodium Saccharin | .10 |
| 16 | Sorbitol 70 | 35 | Sodium saccharin | .07 |
| 17 | Sorbitol 70 & Lycasan | 25/10 | Sodium saccharin | .07 |

| EXAMPLE # | HUMECTANT | (%) | VISCOSIFIER | (%) |
|---|---|---|---|---|
| 2 | Glycerine/propylene glycol | 5/10 | CMC 7 MF | 3.5 |
| 3 | Glycerine/propylene glycol | 5/10 | CMC 7 LF | 8.0 |
| 4 | Glycerine/propylene glycol | 5/10 | Methocel K4M | 2.0 |
| 5 | Glycerine/propylene glycol | 5/10 | Carragenan | 1.0 |

TABLE I-continued

| # | | | | |
|---|---|---|---|---|
| 6 | Propylene glycol | 20 | CMC 9M31F | 2.5 |
| 7 | Glycerin | 10 | Gum Arabic | 5.0 |
| 8 | Glycerin propylene glycol | 7/13 | Klucel GF | 5.0 |
| 9 | Glycerin propylene glycol | 7/13 | CMC 7 LF | 6.0 |
| 10 | Glycerin | 10 | CMC 9M31F | 2.0 |
| 11 | Glycerin | 10 | CMC 9M31F | 3.0 |
| 12 | Glycerin | 10 | CMC 7 MF | 3.0 |
| 13 | Glycerin | 10 | CMC 7 MF | 4.0 |
| 14 | Glycerin | 15 | CMC 7 MF | 5.0 |
| 15 | Glycerin propylene glycol | 10/5 | CMC 9M31F | 2.0 |
| 16 | Propylene glycol | 20 | Klucel GF | 4.0 |
| 17 | Glycerin | 10 | Methocel K4M | 3.0 |

| EXAMPLE # | PRESERVATIVE | (%) |
|---|---|---|
| 2 | Methyl parabenz, propyl parabenz, potassium sorbate | .15/.05/.15 |
| 3 | Methyl parabenz, propyl parabenz, potassium sorbate | .15/.05/.15 |
| 4 | Methyl parabenz, propyl parabenz, potassium sorbate | .15/.05/.15 |
| 5 | Methyl parabenz, propyl parabenz, potassium sorbate | .15/.05/.15 |
| 6 | Sodium Benzoate | .25 |
| 7 | Methyl parabenz, propyl parabenz | .15/.05 |
| 8 | Potassium sorbate | .25 |
| 9 | Potassium sorbate | .10 |
| 10 | Methyl parabenz, propyl parabenz, potassium sorbate | .15/.05/.15 |
| 11 | Methyl parabenz, propyl parabenz, potassium sorbate | .15/.05/.15 |
| 12 | Methyl parabenz, propyl parabenz, potassium sorbate | .15/.05/.15 |
| 13 | Methyl parabenz, propyl parabenz, potassium sorbate | .15/.05/.15 |
| 14 | Sodium benzoate | .25 |
| 15 | Potassium sorbate | .15 |
| 16 | Potassium sorbate | .15 |
| 17 | Potassium sorbate | .15 |

| EXAMPLE # | FLAVOR | (%) | pH* | DEIONIZED WATER |
|---|---|---|---|---|
| 2 | IFF: 252, 453, 244 | .45/.15/.15 | 4.5 | 44.72 |
| 3 | IFF: 252, 453, 244 | .45/.15/.15 | 5.5 | 49.25 |
| 4 | IFF: 252, 453, 244 | .45/.15/.15 | 5.0 | 39.75 |
| 5 | IFF: 252, 453, 244 | .45/.15/.15 | 5.0 | 49.10 |
| 6 | IFF: 252, 453, 244 | .10 | 4.0 | 57.85 |
| 7 | IFF: 252, 453, 244 | .10 | 6.0 | 52.65 |
| 8 | IFF: 252, 453, 244 | .10 | 5.0 | 65.40 |
| 9 | IFF: 252, 453, 244 | .10 | 4.5 | 41.30 |
| 10 | IFF 252 | .5 | 5.0 | 45.00 |
| 11 | IFF 252 | .5 | 4.5 | 53.95 |
| 12 | IFF 252 | .5 | 4.0 | 63.85 |
| 13 | IFF 252 | .5 | 5.5 | 62.97 |
| 14 | IFF 261 | .1 | 3.5 | 37.50 |
| 15 | IFF 261 | .2 | 4.0 | 51.45 |
| 16 | None | — | 5.0 | 38.68 |
| 17 | None | — | 5.0 | 50.73 |

*pH adjusted with citric acid or baking soda as required. Lycasan brand, hydrogenated glucose syrup (Rochette).

EXAMPLE 18

Several gel formulations of the present invention suitable for the cleaning and massaging of gums of endentulous persons were prepared.

These gels had the following formulation, where percentages are by weight:

| Compound | Percent |
|---|---|
| Pluronic F-127 | 2.00 |
| Silicone AF30 | 0.4 |
| Glycerin | 5.00 |
| Sorbitol-70 | 34.00 |
| Flavor | 0.5 |
| Propylene glycol | 10.00 |
| Potassium sorbate | 0.15 |
| Methyl parabenz | 0.15 |
| Propyl parabenz | 0.05 |
| Sodium saccharin | 0.075 |
| Aqueous saturated citric acid solution | (adjusted to pH of 5) |
| Viscosifier | (type and concentration varies as described below) |
| Deionized water | Balance |

A mixing vessel was charged with water, potassium sorbate, methyl parabenz, propyl parabenz, sodium saccharin and Sorbiton-70, while stirring, and then, the mixture was added to a Waring Blender. The pH was adjusted to 5.0 with an aqueous saturated citric acid solution.

The Pluronic F-127 and Silicone AF30 were heated and stirred to effect a hot-melt emulsion. Flavor was added to the hot-melt emulsion. The flavor, hot-melt emulsion was slowly added with vigorous agitation to a Waring Blender. (390 watts)

A vessel was charged with propylene glycol and glycerin with stirring while the solid viscosifier was added. The resulting suspension was added slowly to the rapidly stirred Waring Blender, stirring was continued for 15 minutes and then the resultant gel was transferred to tubes and/or jars for testing and use.

Using the procedure and general formula described above, various viscosifiers were used at one or more concentrations to prepare a series of gels suitable for cleaning and massaging the gums of endentulous persons. Specifically, CMC7MF at 3%, CMC71F at 1.5% and CMC9M31F at 2.5% by weight and were added to a sample of the formula described above to prepare a series of gels suitable for cleaning, massaging and conditioning the gums of endentulous persons. All of the resultant gel formulations of the present invention were useful as gum cleaning, massaging and conditioning gels for endentulous persons.

Examples illustrative of various gels of the present invention suitable for cleaning and massaging gums of endentulous persons can be obtained from the gels set forth in Table I, by adjusting the artificial sweetener:natural sweetener ratio to accommodate adult taste preference and by substituting mouth-freshening flavors in the range of 0.05 to 2.0% by weight such as oil of spearmint, oil of peppermint, oil of clove, and complex flavors such as IFF vanillamint 101
IFF Spearmint 744,
IFF Natural ming 619
IFF Spearmint 082 and the like.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of manufacturing an oral hygiene gel suitable for cleaning, massaging and conditioning gums of babies and endentulous persons, wherein:
A. said gel is free from:
1. abrasive,
2. analgesic, and
3. substances that alter the microflora balance of the oral cavity;
B. said gel consists essentially of
1. a nonionic surfactant,
2. a coating substance insoluble in said surfactant, wherein the weight ratio of said nonionic surfactant to said coating substances is from between about 20:1 to about 2:1; and
3. a viscosifier; and
C. said gel is characterized as:
1. stable,
2. ingestible,
3. non-foaming,
4. substantive to the gums of babies and endentulous persons,
5. disruptive towards the formation of plaque-like films on the gums of babies and endentulous persons, and having
6. a pH of from between about 3 and about 10;
said method comprising the steps of:
1. emulsifying said coating substance in said surfactant at a temperature above the melt temperature of said surfactant,
2. adding said viscosifier to an appropriate carrier, and
3. mixing the hot-melt emulsion with the viscosifier/carrier to form a gel.

2. The method of manufacturing an oral hygiene get according to claim 1 wherein:
a. flavorants are added to the mixture in the emulsifying step,
b. preservatives are added to the viscosifier/carrier mixture and the carrier for the biscosifier is propylene glycol, and
c. mixing of the hot-melt emulsion and viscosifier/-propylene glycol is carried out in the presence of a mixture of water, soribtol, glycerin, potassium sorbate, sodium saccharin and citric acid to form a gel having a pH of about 5.

3. The method according to claim 2, wherein the nonionic surfactant is a mixture of ethylene oxide and propylene oxide poloxamers and the coating substance is a polydimethylsiloxane, and the viscosifier is carboxymethylcellulose.

4. The method according to claim 2 wherein the concentration of nonionic surfactant is from between about 0.1% and about 10% by weight.

5. A method according to claim 1 wherein the nonionic surfactant is selected from mixtures of polyoxyalkylene poloxamers.

6. The method according to claim 5 wherein said poloxamers are mixtures of polyoxypropylene and polyoxyethylene compounds.

7. The method according to claim 1 wherein the coating substance is selected from the group consisting of silicones, polyalkysiloxanes and mixtures thereof.

8. The method according to claim 7, wherein the concentration of coating substance is from between about 0.1% and about 0.5% by weight.

9. The method according to claim 1 wherein the polyalkysiloxanes are polydimethysiloxanes.

10. The method according to claim 1 wherein the viscosifier is selected from the group of cellulose ethers consisting of sodium carboxymethylcellulose, hydroxypropylcellulose, and mixtures thereof.

11. The method according to claim 10, wherein the concentration of viscosifier is from between about 0.5% and about 10% by weight.

12. The method according to claim 1 wherein the pH if from between about 4.0 and about 8.5, and the weight ratio of nonionic surfactant to coating composition is from between about 20:1 and about 2:1.

13. The method according to claim 1 wherein the surfactant is a poloxamer of ethylene oxide and propylene oxide at about 2% by weight, the coating substance is a polydimethylsiloxane at about 0.12% by weight and the viscosifier is carboxymethylcellulose at about 2.5% by weight.

* * * * *